(12) United States Patent
Velasco Varo et al.

(10) Patent No.: US 9,375,023 B2
(45) Date of Patent: Jun. 28, 2016

(54) SUNFLOWER OIL WITH HIGH HEAT STABILITY

(75) Inventors: Leonardo Velasco Varo, Cordova (ES); Jose Maria Fernández Martínez, Cordova (ES); Begoña Perez Vich, Cordova (ES)

(73) Assignee: Consejo Superior De Investigaciones Cientificas, Madrid (ES)

( * ) Notice: Subject to any disclaimer, the term of this patent is extended or adjusted under 35 U.S.C. 154(b) by 544 days.

(21) Appl. No.: 12/808,657

(22) PCT Filed: Nov. 27, 2008

(86) PCT No.: PCT/ES2008/070220
§ 371 (c)(1),
(2), (4) Date: Aug. 9, 2010

(87) PCT Pub. No.: WO2009/080858
PCT Pub. Date: Jul. 2, 2009

(65) Prior Publication Data
US 2011/0061138 A1 Mar. 10, 2011

(30) Foreign Application Priority Data
Dec. 21, 2007 (ES) .................................. 200703417

(51) Int. Cl.
| | | |
|---|---|---|
| *A01H 5/10* | (2006.01) | |
| *C10M 105/36* | (2006.01) | |
| *C10L 1/18* | (2006.01) | |
| *C07C 69/02* | (2006.01) | |
| *A23D 9/007* | (2006.01) | |
| *A23K 1/16* | (2006.01) | |
| *C11B 1/10* | (2006.01) | |
| *C11C 3/00* | (2006.01) | |

(52) U.S. Cl.
CPC *A23D 9/007* (2013.01); *A01H 5/10* (2013.01); *A23K 1/164* (2013.01); *C11B 1/10* (2013.01); *C11C 3/003* (2013.01); *C10G 2300/1014* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 5,872,271 A | 2/1999 | Cole et al. | |
| 6,388,113 B1 | 5/2002 | Martinez Force et al. | |
| 6,953,882 B2 * | 10/2005 | Martinez Force et al. | ..... 800/322 |
| 2002/0183533 A1 | 12/2002 | Martinez Force et al. | |
| 2004/0088758 A1 | 5/2004 | Martinez Force et al. | |
| 2006/0026714 A1 | 2/2006 | Martinez-Force et al. | |

FOREIGN PATENT DOCUMENTS

| | | |
|---|---|---|
| EP | 0965631 | 12/1999 |
| EP | 1616481 | 1/2006 |
| WO | 9520313 | 8/1995 |
| WO | 0074469 | 12/2000 |
| WO | WO 2004089068 A1 | 10/2004 |
| WO | WO 2005046315 A1 | 5/2005 |

OTHER PUBLICATIONS

Ordonez et al. (Bioresour Technol., 78:187-190, 2001).*
Velasco et al., Identification and Genetic Characterization of New Sources of Beta-and Gamma-Tocopherol in Sunflower Germplasm Helia 26 Nr. 348, pp. 17-24. (2003).
Warner, K., "Increasing gamma- and delta-tocopherols in oils improves oxidative stability", Lipid Technology, vol. 19, No. 10, pp. 229-231 (2007).

* cited by examiner

*Primary Examiner* — Vinod Kumar
(74) *Attorney, Agent, or Firm* — Bret E. Field; Bozicevic, Field & Francis LLP

(57) ABSTRACT

The invention relates to a sunflower oil with high heat stability, which is characterized in that between 15% and 45% of the fatty acid total are saturated fatty acids (palmitic acid and stearic acid), between 45% and 75% of the fatty acid total is oleic acid and more than 85% of the tocopherol total corresponds to the sum of gamma-tocopherol and delta-tocopherol. The invention also relates to sunflower seeds that contain an oil with the aforementioned characteristics and sunflower plants which as a result of self-pollination produce seeds with the aforementioned characteristics. In addition, the invention relates to the use of said oil in food and animal feed and for the formulation of biolubricants and biofuels.

26 Claims, No Drawings

SUNFLOWER OIL WITH HIGH HEAT STABILITY

FIELD OF THE ART

The invention is comprised in the agricultural sector, in the food sector, and in the industrial sector. The sunflower oil object of the present invention has a high heat stability, much greater than that of other sunflower oils currently existing. The high heat stability of the oil makes it suitable for domestic and industrial processes requiring or causing high temperatures, both in the food sector (fried foods) and in the industrial sector (biolubricants, biofuels).

STATE OF THE ART

The use of vegetable oils in processes requiring or causing high temperatures demands that the oils have high heat stability or thermal stability. Subjecting the oil to high temperature conditions typical of food preparation processes (frying, baking) or friction processes (lubrication of motors and machinery) causes a series of oil degrading processes, such as oxidation, polymerization, hydrolysis, cycling, and isomerization, which result in the formation of products with unpleasant smells and flavors and with negative properties from the nutritional point of view (Bastida and Sánchez Muñiz, Thermal oxidation of olive oil, sunflower oil and a mix of both oils during forty discontinuous domestic fryings of different foods. *Food Science and Technology International*, 7:15-21, 2001). The occurrence of these oil degrading processes is lower, and therefore the useful life of the oil is greater, the greater its heat stability.

The heat stability of vegetable oils is mainly determined by its degree of unsaturation and by the presence therein of substances with antioxidant properties, which protect the oil during heating and delay the occurrence of degrading processes. The degree of unsaturation of the oil is determined by its fatty acid profile. Fatty acids are more susceptible to oxidation as the degree of unsaturation or number of double bonds in its hydrocarbon chain increases. Among the most common fatty acids in vegetable oils, linolenic acid (polyunsaturated, three double bonds) is the most susceptible to oxidation, followed by linoleic acid (polyunsaturated, two double bonds), oleic acid (monounsaturated, one double bond), and stearic and palmitic acids (saturated, without double bonds) (F. B. Padley et al., 1994; Occurrence and characteristics of oils and fats. *The Lipid Handbook*, ed. F. D. Gunstone, J. L. Harwood and F. B. Padley, London: Chapman & Hall, pp. 47-223).

Oil seeds naturally produce substances with antioxidant properties, among which tocopherols stand out. Tocopherols are molecules consisting of a chromanol group and a phytyl side chain. There are four different naturally occurring forms of tocopherols, called alpha-, beta-, gamma-, and delta-tocopherol, differing from one another by the number and position of methyl (Me) groups in the chromanol ring (FIG. 1).

FIG. 1. Chemical structure of tocopherols

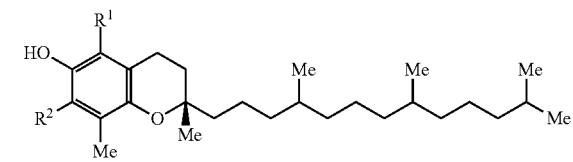

R1 = Me; R2 = Me: Alpha-tocopherol
R1 = Me; R2 = H: Beta-tocopherol
R1 = H; R2 = Me: Gamma-tocopherol
R1 = H; R2 = H: Delta-tocopherol Since they are liposoluble substances, the tocopherols present in oil seeds pass to the oil during the extraction process. Here they have a dual antioxidant action. On one hand, they have in vitro action, i.e., they protect the oil and the products containing them (prepared foods) or derived from it (biofuels, biolubricants) from oxidation during storage and use. On the other hand, tocopherols are bioactive compounds, exerting an important in vivo antioxidant effect, i.e., within the living cell. This in vivo antioxidant activity is known as vitamin E activity (G. Pongracz et al., Tocopherole, Antioxidantien der Natur. *Fat Science and Technology* 97: 90-104, 1995). There are enormous differences among the four types of tocopherols in relation to their in vitro and in vivo antioxidant activity. Therefore, alpha-tocopherol is characterized by having maximum efficacy as an in vivo antioxidant or vitamin E, but its in vitro activity is low in comparison with the other tocopherols. By taking 100% antioxidant activity for alpha-tocopherol as a reference, Pongracz et al. (1995, work mentioned above) determined relative efficiency as in vivo antioxidants of 50% for beta-tocopherol, 25% for gamma-tocopherol, and 1% for delta-tocopherol. In contrast, the relative efficiency as in vitro antioxidants was 182% for beta-tocopherol, 194% for delta-tocopherol, and 285% for gamma-tocopherol.

Sunflower oil naturally has a fatty acid profile consisting of palmitic acid (4-8% of the total fatty acids), stearic acid (2-6% of the total fatty acids), oleic acid (20-45% of the total fatty acids) and linoleic acid (45-70% of the total fatty acids). The relative proportion of oleic and linoleic fatty acids is variable and greatly depends on the temperature during the development of the seed (Fernández-Martínez et al., Performance of near-isogenic high and low oleic acid hybrids of sunflower. *Crop Science* 33: 1158-1163, 1993). A wide range of sunflower lines with modified fatty acid profiles have been developed by means of genetic improvement. The main lines developed and their fatty acid profiles are shown in Table 1.

Table 1. Mean fatty acid composition (%) of the oil from the seed of the main natural or induced sunflower mutants compared to the standard oil (taken from Fernández-Martínez et al., Mejora de la calidad del girasol. *Mejora Genética de la Calidad en Plantas*. Editors: G. Llácer, M. J. Diez, J. M. Carrillo, and M. L. Badenes. Universidad Politécnica de Valencia, pp. 449-471, 2006)

| Mutant or line | Fatty acid composition (%)[1] | | | | |
|---|---|---|---|---|---|
| | 16:0 | 16:1 | 18:0 | 18:1 | 18:2 |
| Standard[2] | 5.7 | — | 5.8 | 20.7 | 64.5 |
| | 6.5 | — | 3.0 | 40.9 | 49.6 |
| Low saturated fatty acid content | | | | | |
| LS-1 | 5.6 | 0.0 | 4.1 | 20.2 | 67.4 |
| LS-2 | 8.6 | 0.0 | 2.0 | 10.8 | 75.0 |
| LP-1 | 4.7 | 0.0 | 5.4 | 23.8 | 63.7 |
| RS1 | 3.9 | 0.0 | 2.6 | 40.1 | 51.8 |
| RS2 | 4.4 | 0.0 | 3.2 | 42.9 | 47.7 |
| High palmitic acid content | | | | | |
| 275HP | 25.1 | 6.9 | 1.7 | 10.5 | 55.8 |
| CAS-5 | 25.2 | 3.7 | 3.5 | 11.4 | 55.1 |
| CAS-12 | 30.7 | 7.6 | 2.1 | 56.0 | 3.1 |
| HP line | 23.9 | 3.4 | 2.0 | 20.4 | 50.7 |
| CAS-37[3] | 29.5 | 12.3 | 1.4 | 5.4 | 38.7 |

-continued

| Mutant | Fatty acid composition (%)[1] | | | | |
|---|---|---|---|---|---|
| or line | 16:0 | 16:1 | 18:0 | 18:1 | 18:2 |
| High stearic acid content | | | | | |
| CAS-3 | 5.1 | 0.0 | 26.0 | 13.8 | 55.1 |
| CAS-4 | 5.4 | 0.0 | 11.3 | 34.6 | 48.0 |
| CAS-8 | 5.8 | 0.0 | 9.9 | 20.4 | 63.8 |
| CAS-14 | 8.4 | 0.0 | 37.3 | 12.4 | 38.0 |
| CAS-19 | 6.8 | 0.0 | 15.3 | 21.5 | 56.4 |
| CAS-20 | 5.7 | 0.0 | 7.7 | 35.9 | 50.5 |
| High oleic acid content | | | | | |
| Pervenets | —[3] | — | — | 79.3 | 14.8 |
| M-4229 | 3.4 | — | 4.1 | 86.1 | 3.9 |
| M-3067 | 3.9 | — | 5.2 | 54.6 | 33.9 |
| High linoleic acid content | | | | | |
| F6 sel. | — | — | — | — | 77.3 |
| 2698-1 | — | — | — | — | 78.0 |

[1]16:0 = palmitic acid; 18:0 = stearic acid; 16:1 = palmitoleic acid 18:1 = oleic acid; 18:2 = linoleic acid.
[2]Data of standard crops obtained in cold and warm environments, respectively.
[3]Data not provided by the authors Sunflower oil is characterized by naturally having a tocopherol profile mainly consisting of alpha-tocopherol, representing more than 90% of the total tocopherols, the proportions of beta-, gamma-, and delta tocopherol being less than 5% of the total tocopherols (Demurin et al., Genetic variability of tocopherol composition in sunflower seeds as a basis of breeding for improved oil quality. *Plant Breeding* 115: 33-36, 1996). Sunflower lines with a high beta-tocopherol content (more than 50% of the total tocopherols), a high gamma-tocopherol content (more than 90% of the total tocopherols), and a high delta-tocopherol content (more than 65% of the total tocopherols) have been developed by means of genetic improvement (Fernández-Martínez et al., 2006, work mentioned above).

Sunflower oils with a low degree of unsaturation, mainly consisting of saturated fatty acids (stearic acid and palmitic acid) and monounsaturated fatty acids (oleic acid) have greater heat stability than standard sunflower oil, with a higher degree of unsaturation (R. Garcés et al., High stable vegetable oils. WO99/64546). Likewise, sunflower oils in which alpha-tocopherol has been partially substituted with other tocopherols with a higher in vitro antioxidant power, mainly gamma- and delta-tocopherol, have greater heat stability than standard sunflower oil, with a high alpha-tocopherol content (L. Velasco and J. M. Fernández-Martínez, Sunflower Seeds with High Delta-tocopherol Content. WO2004/089068). No vegetable sunflower material the seeds of which produce an oil with a low degree of unsaturation, determined by a high saturated and monounsaturated fatty acid content, and with a low alpha-tocopherol content in its tocopherol profile has been developed until now.

DESCRIPTION OF THE INVENTION

Brief Description

The present invention relates to a sunflower oil extracted from sunflower seeds having a series of properties in its fatty acid profile and in its tocopherol profile conferring it with greater heat stability compared to any other sunflower oil developed up until now. The sunflower oil object of this invention is characterized by a saturated fatty acid (palmitic acid and stearic acid) content between 15% and 45% of the total fatty acids present in the oil, an oleic acid content between 45% and 75% of the total fatty acids. This oil can also have a palmitoleic acid content greater than 5% of the total fatty acids, mainly when the predominant saturated fatty acid is palmitic acid. The linoleic acid content is less than 10%, preferably less than 5% of the total fatty acids present in the oil. Likewise, the sum of gamma- and delta-tocopherol represents more than 85% of the total tocopherols present in the oil, the alpha-tocopherol content being less than 15% of the total tocopherols, and the total tocopherol content of this oil is between 500 mg per kg of oil and more than 1250 mg per kg of oil.

It is an oil with a high heat stability, its oil stability index (measured in a Rancimat model 743 apparatus (Metrohm AG, Herisau, Switzerland) after an induction period of 10 hours at a temperature of 110° C. on the unrefined oil) being between 35 hours and more than 120 hours.

The present invention also relates to the sunflower seeds containing an oil with the mentioned characteristics, and the sunflower plants which, upon being self-fertilized, produce seeds with the mentioned characteristics. There are currently no sunflower seeds producing an oil with the combination of characteristics in the fatty acid and tocopherol profiles such as the one achieved in the seeds object of the present invention.

The use of the oil for human and animal foods, and for the production of biolubricants and biofuels is also another object of the present invention.

DETAILED DESCRIPTION

The present invention relates to a sunflower oil extracted from seeds produced by plants of the *Helianthus annuus* L. species which produce a special oil type with characteristics of its fatty acid profile and tocopherol profile conferring it with exceptional heat stability.

The mentioned oil is characterized by a high saturated fatty acid, palmitic acid and stearic acid, content (15-45% of the total fatty acids in the oil), a high oleic acid content (45-75% of the total fatty acids), and a high gamma- and delta-tocopherol sum content (greater than 85% of the total tocopherols present in the oil). The combination of these three properties confers to the oil high heat stability.

This oil can also have a palmitoleic acid content greater than 5% of the total fatty acids, mainly when the predominant saturated fatty acid is palmitic acid, with a linoleic acid content less than 10%, preferably less than 5% of the total fatty acids present in the oil.

In a particular embodiment of the invention, the palmitoleic acid content is greater than 10% of the total fatty acids in the oil.

The maximum oil stability of the oil is conferred by the saturated fatty acids. However, a very high content of these fatty acids in the oil determines a low smoke point in fried foods and a low oil nutritional value. The oleic acid confers to the oil lower oil stability than the saturated fatty acids, but a higher smoke point and a higher nutritional value. Gamma- and delta-tocopherols confer to the oil an oil stability greater than that conferred by beta- and alpha-tocopherols.

The alpha-tocopherol content of the oil of the invention is less than 15% of the total tocopherols present in the oil. The total tocopherol content can also range between 500 mg per kg of oil and more than 1250 mg per kg of oil.

This oil was obtained by recombining the following individual characters, already previously developed in sunflower:

a) High saturated fatty acid content. There are several sunflower lines having between 15% and 45% of the fatty acids in the oil of their seeds in the form of saturated fatty acids, both in the form of palmitic acid (16:0) and in the form of stearic acid (18:0). Two types of lines were used: 1) high stearic, the stearic acid content of which is between 15% and 45% of the total fatty acids in the oil of the seeds, and 2) high palmitic, the palmitic acid content of which is between 15% and 45% of the total fatty acids in the oil of the seeds and the palmitoleic acid content (16:1) of which is between 5% and 15% of the total fatty acids in the oil of the seeds.

b) High oleic acid content (18:1). The sunflower lines referred to as "high oleic" used have between 85% and 95% of the fatty acids in the oil of their seeds in the form of oleic acid. The linoleic acid content (18:2) is between 2% and 10% of the total fatty acids in the oil of their seeds.

c) High gamma-tocopherol and delta-tocopherol sum content. This character is present in several sunflower lines, in which the sum of both tocopherols represents more than 85% of the total tocopherols present in the seeds. Two types of lines were used: 1) high gamma-tocopherol, in which the gamma-tocopherol content represents more than 85% of the total tocopherols in the seeds, being able to reach a value of up to 99% of the total tocopherols in the seeds, and 2) high delta-tocopherol, in which the delta-tocopherol content represents more than 65% of the total tocopherols in the seeds and the gamma-tocopherol content represents more than 20% of the total tocopherols in the seeds, the sum of delta-tocopherol and gamma-tocopherol being greater than 85% of the total tocopherols in the seeds, being able to reach a value of up to 99% of the total tocopherols in the seeds. The seeds of both types of lines result in an oil the total tocopherol content of which is between 500 and 1500 mg per kg of oil, with the tocopherol profiles aforementioned.

Since these are characters with high genetic complexity, the recombination was performed in two steps which are described below:

1) Recombination of the "high saturated fatty acid content" and "high oleic acid content" characters.

Controlled crossbreedings were performed between the lines with high saturated fatty acid (palmitic acid and stearic acid) content and the line with high oleic acid content, and the $F_1$ hybrid seed was obtained. This seed germinated and the corresponding plants were self-fertilized to obtain the $F_2$ seed, which showed segregation for both characters. Since each of the individual characters is controlled by 1-3 genes, most of them recessive, it was necessary to analyze a mean of 100 $F_2$ seeds of each of the crossbreedings to obtain a seed having the combination of the characters sought, i.e., high saturated fatty acid content and high oleic acid content. The low frequency of occurrence of seeds which combined the two characters made it necessary to analyze an average of 2,000 seeds of each of the crossbreedings to obtain a sufficient number of seeds with the two combined characters.

In order for the combination of modified characters of the fatty acid profile to be commercially useful, the characters must be inheritable and they must be expressed independently of the environmental conditions in which the plants are cultivated. For this reason, a selection process was conducted which led to fixing the characters and to verifying their stability under different environmental conditions. To that end, the selected $F_2$ seeds were sown and the genetic stability of the combined characters was confirmed by means of analyzing the $F_3$ seeds originating from the self-fertilization of each of the $F_2$ plants, and of $F_4$ seeds originating from a high number of $F_3$ plants cultivated in several environments.

As a result of this first step, plants were obtained the seeds of which contain a high saturated fatty acid content, between 15% and 45% of the total fatty acids present in the oil, a high oleic acid content, between 45% and 75% of the total fatty acids, and a low linoleic acid content, less than 10% of the total fatty acids.

2) Recombination of the new "high saturated fatty acid content and high oleic acid content" character with the "high gamma- and delta-tocopherol sum content" character.

In this second step, plants obtained in the previous step 1) were used which recombine a high saturated fatty acid content (15-45% of the total fatty acids present in the oil) and high oleic acid content (45-75% of the total fatty acids present in the oil), as well as plants with a high gamma-tocopherol and delta-tocopherol sum content (more than 85% of the total tocopherols present in the seeds).

After performing controlled crossbreedings between the lines with a high gamma- and delta-tocopherol sum content with $F_3$ plants with a high saturated fatty acid content and high oleic acid content, the $F_1$ hybrid seed was obtained. This seed germinated and the corresponding plants were self-fertilized to obtain the $F_2$ seed, which showed segregation for the three characters object of the recombination, i.e., high saturated fatty acid (palmitic acid and stearic acid) content, high oleic acid content, and high gamma- and delta-tocopherol sum content. Since the sought fatty acid profile is controlled by 4-6 genes, and the sought tocopherol profile is controlled by 1-3 genes, generally recessive, it was necessary to analyze a mean of 400 $F_2$ seeds of each of the crossbreedings to obtain a seed having the combination of the sought characters, i.e., high saturated fatty acid content, high oleic acid content, and high gamma- and delta-tocopherol sum content. The low frequency of occurrence of seeds which combined the two characters made it necessary to analyze an average of 5,000 seeds of each of the crossbreedings to obtain a sufficient number of seeds with the two combined characters.

In order for the combination of modified characters of the fatty acid profile to be commercially useful, they must be inheritable and they must be expressed independently of the environmental conditions in which the plants are cultivated. For this reason, a selection process was conducted which led to fixing the characters and to verifying their stability under different environmental conditions. To that end, the selected $F_2$ seeds were sown and the genetic stability of the combined characters was confirmed by means of analyzing the $F_3$ seeds of each of the $F_2$ plants, and of $F_4$ seeds originating from a high number of $F_3$ plants. These plants were cultivated in different environments, which served to confirm that the simultaneous expression of high saturated fatty acid content, high oleic acid content, and high gamma-tocopherol and delta-tocopherol sum content is the result of a fixed and stable genetic inheritance which is expressed independently of the cultivation conditions of the plants.

As a result of this second step, plants were obtained the seeds of which contain a high saturated fatty acid content, between 15% and 45% of the total fatty acids present in the oil, a high oleic acid content, between 45% and 75% of the total fatty acids, a gamma-tocopherol and delta-tocopherol sum content greater than 85% of the total tocopherols present in the oil. When the source of saturated fatty acids was a line with a high palmitic acid content (15-45% of the total fatty acids in the oil), the presence of a palmitoleic acid content greater than 5% of the total fatty acids in the oil was also observed.

Taking into account the range in the fatty acid (palmitic, stearic and oleic acid) and tocopherol content of the sunflower lines used in the different recombination steps, the particular embodiments of the invention obtained include oils with a stearic acid content greater than 15%, greater than 25% and greater than 35% of the total fatty acids present in the oil. Other particular embodiments of the invention have a palmitic acid content greater than 15%, greater than 25% and greater than 35% of the total fatty acids present in the oil.

In two other particular embodiments of the invention, the oil of the invention has a gamma-tocopherol content greater than 85% and greater than 95% of the total tocopherols present in the oil.

In other particular embodiments of the invention, the oil has a delta-tocopherol content greater than 25%, greater than 55% and greater than 75% of the total tocopherols present in the oil.

Due to the fatty acid profile with a low unsaturation level, which is the main cause of the oxidation and low heat stability of the vegetable oils, and to the presence of a high proportion of tocopherols with a strong protective action against oxidation and the effect of the high temperature, the oil extracted from the seeds produced by the plants described above has exceptional heat stability, much greater than that of any conventional sunflower oil, and also greater than that of any other sunflower oil which only has the fatty acid profile or the tocopherol profile modified.

The oil stability index (OSI) of the oil object of the present invention, measured in a Rancimat model 743 apparatus (Metrohm AG, Herisau, Switzerland) after an induction period of 10 hours at a temperature of 110° C. on the unrefined oil ranges between 35 and 120 hours.

The thermo-oxidative degradation of an oil is evaluated by studying the degradation of the tocopherols present in said oil and the occurrence of polar compounds and polymers during heating. The oil object of the present invention has a thermo-oxidative degradation less than that of the oil obtained from the seeds used as parent seeds, having a lower percentage (half) of the formation of polymers and polar compounds.

Given these technical characteristics of the oil of the invention, with a high oil stability and high resistance against thermo-oxidative degradation, this oil can suitably be used in human and/or animal foods. The oil of the invention can also be used in the production of biolubricants and/or biofuels.

In a particular embodiment of the invention, the oil of the invention is obtainable from the extraction from sunflower seeds of the seed line IAS-1265, deposited on 20 Mar. 2007 in the NCIMB (National Collection of Industrial, Marine and Food Bacteria) Ltd., Aberdeen, Scotland, with accession number NCIMB-41477.

The mixtures of oils containing the oil of the invention are also an object of the present invention, as well as the flour obtained as the residue of the extraction process for extracting the oil from the sunflower seeds.

Another object of the present invention is the sunflower seeds containing an oil with the characteristics of the oil of the invention. They are seeds resulting in plants which, after their germination, contain in their seeds, upon being self-fertilized, an oil with the characteristics of the oil of the invention, independently of the cultivation conditions of the plants. In a particular embodiment the seeds of the invention originate from sunflower line IAS-1265, deposited on 20 Mar. 2007 in the seed bank of NCIMB Ltd., Aberdeen, Scotland, with the accession number NCIMB-41477. The seeds object of the present invention can be used for obtaining the oil of the invention.

The sunflower plants (*Helianthus annuus* L.) which, upon being self-fertilized, produce seeds containing the oil of the invention are also another object of the present invention.

Embodiments

Obtaining the Seeds 5.1. Recombination of the "High Saturated Fatty Acid Content" and "High Oleic Acid Content" Characters Forty-eight seeds of each of the sunflower lines NP-40, with high palmitic acid content in the oil (greater than 15% of the total fatty acids), developed by means of chemical mutagenesis, and BSD-2-423, with a high oleic acid content in the oil (greater than 85% of the total fatty acids) were taken randomly and the acid composition or profile in the oil of each of the individual seeds was analyzed. Since the analysis of the seeds cannot be destructive, because after the analysis the seeds must be able to germinate, the analysis was conducted by means of the half seed process. Said process consists of cutting a small portion of the seed distal to the embryo, such that the cut does not affect the germinating capacity of the seed. The cut portion is then analyzed for its fatty acid profile by means of gas chromatography of the methyl esters of the fatty acids (R. Garcés and M. Mancha, One-step lipid extraction and fatty acid methyl esters preparation from fresh plant tissues. *Analytical Biochemistry*, 211:139-143, 1993), and the rest of the seed containing the embryo is stored in optimal conditions in order for its germination to occur depending on the analytical results.

Once the fatty acid profile of each of the seeds was confirmed, said seeds germinated and the corresponding plants were cultivated in a greenhouse and controlled crossbreedings between NP-40 plants and BSD-2-423 plants were performed. These crossbreedings consist of removing the stamina or male organs of the flowers at dawn, before the anthers open to release the pollen, in plants which are going to be used as female parents, followed by the artificial pollination using pollen of the plants which are going to be used as male parents. In this example, the BSD-2-423 plants were used as the female parent and the NP-40 plants were used as the male parent, although the same result is obtained using the parents in the opposite sense.

The hybrid seeds resulting from the crossbreedings, referred to as $F_1$ seeds, were analyzed for their fatty acid profile by means of the half seed process explained above. The mean palmitic acid content in the $F_1$ seeds was 7.3% of the total fatty acids in the oil, compared to 30.0% in the seeds of the NP-40 plants and 3.5% in the seeds of the BSD-2-423 plants. The mean oleic acid content of the $F_1$ seeds was 69.8% of the total fatty acids in the oil, compared to 8.0% in the NP-40 seeds and 89.6% in the BSD-2-423 seeds.

150 $F_1$ seeds germinated and the corresponding plants were self-fertilized to obtain the $F_2$ seeds, which were analyzed for their fatty acid profile. 2,348 $F_2$ seeds were analyzed, segregation for the palmitic acid and oleic acid contents being observed. The palmitic acid content in the $F_2$ seeds ranged between 3.1% and 37.8% of the total fatty acids in the oil. The oleic acid content in the $F_2$ seeds showed a variation range between 6.9% and 92.2% of the total fatty acids in the oil. Out of the 2,348 analyzed seeds analyzed, 104 of them showed a combination of high palmitic acid content, greater than 15% of the total fatty acids, and high oleic acid content, greater than 45% of the total fatty acids in the oil. Out of these 104 seeds, that seed with a higher palmitic acid content presented a palmitic acid content of 34% and an oleic acid content of 55% of the total fatty acids, whereas that seed with a higher oleic acid content had a palmitic acid content of 18% and an oleic acid content of 73% of the total fatty acids.

The selected $F_2$ seeds were sown and the genetic stability of the combined characters was confirmed by means of analyzing the F₃ seeds of each of the F₂ plants. The analysis of a total of 3,744 F₃ seeds resulted in a fatty acid composition of the oil of the seeds consisting of a mean content of 27.7%±3.4% (mean±standard deviation) palmitic acid, 7.2%±1.7% palmitoleic acid, 1.4%±0.3% stearic acid, 59.8%±4.9% oleic acid, and 3.9%±1.0% linoleic acid.

5.2. Recombination of the "High Saturated Fatty Acid Content and High Oleic Acid Content" Characters with the "High Gamma- and Delta-Tocopherol Sum Content" Character Forty-eight F₃ seeds obtained in the previous step were taken, which seeds combined a high palmitic acid content (greater than 15%) and a high oleic acid content (greater than 45%), and 48 seeds of the T2100 line, with high gamma-tocopherol content (greater than 85%), and for each seed both the acid composition or profile in the oil and the tocopherol composition or profile of each of the individual seeds was analyzed. This analysis was conducted by means of the half seed process described above. The cut portion of the seed was divided into two halves and the fatty acid profile was analyzed in one half by means of gas chromatography of the methyl esters of the fatty acids (R. Garcés and M. Mancha, 1993, work mentioned above) and the tocopherol profile was analyzed in the other half by means of high performance liquid chromatography—HPLC (F. Goffman et al., Quantitative determination of tocopherols in single seeds of rapeseed, *Brassica napus* L., *Fett/Lipid* 101:142-145, 1999).

Once the fatty acid and tocopherol profile of each of the seeds was confirmed, said seeds germinated and the corresponding plants were cultivated in a greenhouse and controlled crossbreedings between plants originating from F₃ seeds and T2100 plants were performed similarly to that described in section 5.1. The F₁ seeds were analyzed for their fatty acid and tocopherol profiles. The mean palmitic acid content in the F₁ seeds was 6.8% of the total fatty acids in the oil, compared to 28.9% in the seeds of the NP-40 plants and 3.2% in the seeds of the T2100 plants. The oleic acid content of the F₁ seeds was 72.6.8% of the total fatty acids in the oil, compared to 90.3% in the BSD-2-423 seeds and 12.1% in the seeds of T2100. The gamma-tocopherol content of the F₁ seeds was 1.2% of the total tocopherols, compared to 0.0% in the NP-40 and BSD-2-423 seeds used as control, and 99.2% in the T2100 seeds.

100 F₁ seeds germinated and the corresponding plants were self-fertilized to obtain the F₂ seeds, which were analyzed for their fatty acid profile. 8,952 F₂ seeds were analyzed, segregation for the palmitic acid, oleic acid and gamma-tocopherol contents being observed. The palmitic acid content in the F₂ seeds ranged between 2.2% and 37.6% of the total fatty acids in the oil. The oleic acid content in the F₂ seeds showed a variation range between 5.8% and 94.2% of the total fatty acids in the oil. The gamma-tocopherol content showed a variation between 0.0% and 99.6% of the total tocopherols in the seeds. Out of the 8,952 seeds analyzed, 51 of them showed a combination of high palmitic acid content, greater than 15% of the total fatty acids, high oleic acid content, greater than 45% of the total fatty acids in the oil, and high gamma-tocopherol content, greater than 85% of the total tocopherols in the seed.

The selected F₂ seeds were sown and the genetic stability of the combined characters was confirmed by means of analyzing the F₃ seeds of each of the F₂ plants. The analysis of a total of 3,204 F₃ seeds resulted in a fatty acid composition of the oil of the seeds consisting of a mean content of 28.9%±3.3% (mean±standard deviation) palmitic acid, 7.3%±1.1% palmitoleic acid, 1.6%±0.5% stearic acid, 52.5%±3.9% oleic acid, and 4.2%±0.7% linoleic acid, and a composition of the tocopherol fraction consisting of 2.8%±1.3% alpha-tocopherol, 96.6%±1.8% gamma-tocopherol, and 0.6%±0.2% delta-tocopherol.

Extraction of the Oil

A batch of 150 g of F₃ seeds was used to extract the oil using petroleum ether (boiling point 40-60° C.) and a Soxhlet extraction system, following the process of the *Asociación Española de Normalización* (Spanish Standardization Association) (Catálogo de normas UNE. Madrid, 1991). The oil was analyzed for its fatty acid and tocopherol composition, resulting in a fatty acid composition consisting of 29.2% palmitic acid, 7.5% palmitoleic acid, 1.7% stearic acid, 52.4% oleic acid, and 4.2% linoleic acid, and a composition of the tocopherol fraction consisting of 2.4% alpha-tocopherol, 96.4% gamma-tocopherol, and 1.2% delta-tocopherol.

Technical Characteristics of the Oil Obtained a) Study of the Oil Stability Index (OSI) in Different Types of Sunflower Oils The oil stability index (OSI) was measured after heating at 110° C. for 10 hours following the standard protocol of the American Oil Chemists' Society (Official Methods and Recommended Practices of the American Oil Chemists' Society, 4th edition, AOCS, Champaign, Ill., U.S.A., 1994) in the following types of sunflower oil:

Oil 1: Standard sunflower oil (standard fatty acid and tocopherol profiles)

Oil 2: Oil with high oleic acid content and standard tocopherol profile

Oil 3: Oil with high palmitic acid content, high oleic acid content, and standard tocopherol profile Oil 4: Oil object of the present invention, with high palmitic acid content, high oleic acid content, and modified tocopherol profile (high gamma-tocopherol content).

The fatty acid and tocopherol composition of the four types of sunflower oil, as well as the OSI after heating at 110° C. for 10 hours, are shown in Table 2:

TABLE 2

Fatty acid and tocopherol composition and their OSI values after heating at 110° C. for 10 hours of four types of sunflower oil:

| | Fatty acids (%)[a] | | | | | Tocopherols (%)[b] | | | | |
|---|---|---|---|---|---|---|---|---|---|---|
| Oil | 16:0 | 16:1 | 18:0 | 18:1 | 18:2 | A-T | B-T | G-T | D-T | OSI (h) |
| 1 | 6.9 | 0.0 | 5.8 | 34.1 | 53.2 | 99.9 | 0.1 | 0.0 | 0.0 | 1.2 |
| 2 | 4.3 | 0.0 | 3.1 | 90.4 | 2.2 | 99.9 | 0.1 | 0.0 | 0.0 | 1.5 |
| 3 | 28.2 | 7.8 | 1.7 | 56.9 | 2.1 | 99.9 | 0.1 | 0.0 | 0.0 | 17.1 |
| 4 | 29.2 | 7.5 | 1.7 | 52.4 | 4.2 | 2.4 | 0.0 | 96.4 | 1.2 | 49.5 |

[a] 16:0 = palmitic acid; 18:0=stearic acid; 18:1 = oleic acid; 18:2 = linoleic acid; 16:1 palmitoleic acid
[b] A-T = alpha-tocopherol; B-T = beta-tocopherol; G-T = gamma-tocopherol; D-T = delta-tocopherol b) Study of the Degradation of Tocopherols and the Occurrence of Polar Compounds and Polymers During Heating To study the synergistic effect of the modification of the tocopherol profile of already modified fatty acid profiles in the oil, oils 3 and 4 described in section a) were subjected to a high temperature (180° C.) for a prolonged time period (25 hours), and the following parameters directly related to the thermo-oxidative degradation of the oil were measured:

Total tocopherol content, said tocopherols expressed as total mg of tocopherols per kg of oil, measured according to the standard method of the International Union of Pure and Applied Chemistry (IUPAC, Standard methods for the analysis of oils, fats and derivatives. 1st supplement to 7th edition. Pergamon Press, Oxford, United Kingdom, 1992).

Formation of polar compounds, expressed as the % of the total weight of the oil, measured according to the method described by M. C. Dobarganes et al. (High-performance size exclusion chromatography of polar compounds in heated and non-heated fats, *Fat Science and Technology* 90: 308-311, 1988).

Formation of polymers, expressed as the % of the total weight of the oil, measured according to the standard method of the International Union of Pure and Applied Chemistry (IUPAC, 1992, work mentioned above).

The results are shown in Table 3.

TABLE 3

Total tocopherol content (mg kg$^{-1}$), polar compound content (%) and polymer content (%) of two types of oil after heating at 180° C. for 25 hours.

| | Tocopherols (%)[a] | | | | Tocopherols (mg kg$^{-1}$) | | Polar compounds (%) | | Polymers (%) | |
|---|---|---|---|---|---|---|---|---|---|---|
| Oil | A-T | B-T | G-T | D-T | 0[b] | 25[b] | 0 | 25 | 0 | 25 |
| 3 | 99.9 | 0.1 | 0.0 | 0.0 | 826 | 0 | 3.0 | 21.0 | 0.0 | 8.7 |
| 4 | 2.4 | 0.0 | 96.4 | 1.2 | 808 | 135 | 3.2 | 10.7 | 0.0 | 4.0 |

[a] A-T = alpha-tocopherol; B-T = beta-tocopherol; G-T = gamma-tocopherol; D-T = delta-tocopherol
[b] Indicate the initial levels (0) and those obtained after 25 hours of heating (25) in the conditions indicated above

The invention claimed is:

1. A non-naturally occurring sunflower seed oil with a higher heat stability than a naturally occurring sunflower seed oil, wherein the naturally occurring sunflower seed oil has 4-8% palmitic acid, 2-6% stearic acid, 20-45% oleic acid, and 45-70% linoleic acid of the total fatty acids, and more than 90% alpha-tocopherol of the total tocopherols, and wherein the non-naturally occurring sunflower seed oil is obtained from sunflower seeds that are from seed line IAS-1265, seeds of which seed line were deposited on 20 Mar. 2007 in the NCIMB (National Collection of Industrial, Marine and Food Bacteria) Ltd., Aberdeen, Scotland, with accession number NCIMB-41477 and has a saturated fatty acid content between 15% and 45% of the total fatty acids present in the oil, an oleic acid content between 45% and 75% of the total fatty acids present in the oil, and a gamma-tocopherol and delta-tocopherol sum content greater than 85% of the total tocopherols present in the oil.

2. The non-naturally occurring sunflower seed oil according to claim 1, wherein the non-naturally occurring sunflower seed oil comprises alpha-tocopherol and the alpha-tocopherol content is less than 15% of the total tocopherols present in the oil.

3. The non-naturally occurring sunflower seed oil according to claim 1, wherein the non-naturally occurring sunflower seed oil comprises stearic acid and the stearic acid content is greater than 15% of the total fatty acids present in the oil.

4. The non-naturally occurring sunflower seed oil according to claim 1, wherein the non-naturally occurring sunflower seed oil comprises stearic acid and the stearic acid content is greater than 25% of the total fatty acids present in the oil.

5. The non-naturally occurring sunflower seed oil according to claim 1, wherein the non-naturally occurring sunflower seed oil comprises stearic acid and the stearic acid content is greater than 35% of the total fatty acids present in the oil.

6. The non-naturally occurring sunflower seed oil according to claim 1, wherein the non-naturally occurring sunflower seed oil comprises palmitic acid and the palmitic acid content is greater than 15% of the total fatty acids present in the oil.

7. The non-naturally occurring sunflower seed oil according to claim 1, wherein the non-naturally occurring sunflower seed oil comprises palmitic acid and the palmitic acid content is greater than 25% of the total fatty acids present in the oil.

8. The non-naturally occurring sunflower seed oil according to claim 1, wherein the non-naturally occurring sunflower seed oil comprises palmitic acid and the palmitic acid content is greater than 35% of the total fatty acids present in the oil.

9. The non-naturally occurring sunflower seed oil according to claim 1, wherein the gamma-tocopherol content is greater than 85% of the total tocopherols present in the oil.

10. The non-naturally occurring sunflower seed oil according to claim 1, wherein the gamma-tocopherol content is greater than 95% of the total tocopherols present in the oil.

11. The non-naturally occurring sunflower seed oil according to claim 1, wherein the delta-tocopherol content is greater than 25% of the total tocopherols present in the oil.

12. The non-naturally occurring sunflower seed oil according to claim 1, wherein the delta-tocopherol content is greater than 55% of the total tocopherols present in the oil.

13. The non-naturally occurring sunflower seed oil according to claim 1, wherein the delta-tocopherol content is greater than 75% of the total tocopherols present in the oil.

14. The non-naturally occurring sunflower seed oil according to claim 1, wherein the non-naturally occurring sunflower seed oil comprises palmitoleic acid and the palmitoleic acid content is greater than 5% of the total fatty acids present in the oil.

15. The non-naturally occurring sunflower seed oil according to claim 1, wherein the non-naturally occurring sunflower seed oil comprises palmitoleic acid and the palmitoleic acid content is greater than 10% of the total fatty acids present in the oil.

16. The non-naturally occurring sunflower seed oil according to claim 1, wherein the non-naturally occurring sunflower seed oil comprises linoleic acid and the linoleic acid content is less than 10% of the total fatty acids present in the oil.

17. The non-naturally occurring sunflower seed oil according to any of claims 1 to 16, wherein the total tocopherol content is greater than 500 mg per kg of oil.

18. The non-naturally occurring sunflower seed oil according to claim 1, characterized in that the oil stability index measured after an induction period of 10 hours at a temperature of 110° C. on the unrefined oil is greater than 35 hours, wherein said oil stability index is measured in a Rancimat model 743 apparatus obtained from Methrohm AG, Herisau, Switzerland.

19. The non-naturally occurring sunflower seed oil according to claim 1, wherein the oil stability index measured after an induction period of 10 hours at a temperature of 110° C. on the unrefined oil is greater than 100 hours, wherein said oil stability index is measured in a Rancimat model 743 apparatus obtained from Methrohm AG, Herisau, Switzerland.

20. The non-naturally occurring sunflower seed oil according to claim 1, wherein the fatty acid comprises at least one palmitic acid and stearic acid.

21. The non-naturally occurring sunflower seed oil according to claim 16, wherein the linoleic acid content is less than 5%.

22. The non-naturally occurring sunflower seed oil according to claim 1, wherein the total tocopherol content is greater than 750 mg per kg of oil.

23. The non-naturally occurring sunflower seed oil according to claim 1, wherein the total tocopherol content is greater than 1250 mg per kg of oil.

24. The non-naturally occurring sunflower seed oil according to claim 18, wherein the oil stability index is greater than 50 hours.

25. The non-naturally occurring sunflower seed oil according to claim 18, wherein the oil stability index is greater than 75 hours.

26. The non-naturally occurring sunflower seed oil according to claim 19, wherein the oil stability index is greater than 120 hours.

\* \* \* \* \*